US008942793B2

(12) United States Patent
Eberle et al.

(10) Patent No.: US 8,942,793 B2
(45) Date of Patent: Jan. 27, 2015

(54) METHOD AND SYSTEM FOR ARRHYTHMIA DISCRIMINATION

(71) Applicant: Cardiac Pacemakers, Inc., St. Paul, MN (US)

(72) Inventors: LeAnne M. Eberle, Mahtomedi, MN (US); David L. Perschbacher, Coon Rapids, MN (US); Dan Li, Shoreview, MN (US); Alicia Elaine Byrnes, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/082,909

(22) Filed: Nov. 18, 2013

(65) Prior Publication Data

US 2014/0148717 A1    May 29, 2014

Related U.S. Application Data

(60) Provisional application No. 61/731,163, filed on Nov. 29, 2012.

(51) Int. Cl.
*A61B 5/04* (2006.01)
*A61B 5/0464* (2006.01)
(Continued)

(52) U.S. Cl.
CPC ............. *A61B 5/0464* (2013.01); *A61B 5/7264* (2013.01); *A61N 1/3621* (2013.01); *A61N 1/36114* (2013.01)
USPC .......................................... 600/510; 600/509

(58) Field of Classification Search
CPC . A61B 5/0464; A61B 5/04525; A61B 5/7264
USPC .................................................. 600/509–510
See application file for complete search history.

(56) References Cited

U.S. PATENT DOCUMENTS 7,582,061 B2    9/2009    Li et al.
7,818,056 B2    10/2010    Kim et al.
(Continued)

FOREIGN PATENT DOCUMENTS

WO    WO-9965570 A1    12/1999
WO    WO-2014085125 A1    6/2014

OTHER PUBLICATIONS

"International Application Serial No. PCT/US2013/070564, International Search Report mailed Mar. 3, 2014", 3 pgs.
(Continued)

*Primary Examiner* — Nicole F Lavert
(74) *Attorney, Agent, or Firm* — Schwegman Lundberg & Woessner, P.A.

(57) ABSTRACT

A method and system for discriminating ventricular arrhythmia is disclosed. In an embodiment, the method can include implementing an arrhythmia discrimination algorithm that can discriminate between supraventricular tachycardia (SVT) and ventricular tachycardia (VT) using at least one programmable parameter programmed to a first value. The method can include analyzing an SVT event, where analyzing the SVT event can include sensing a physiological signal during the SVT event and identifying characteristics of the sensed physiological signal. The method can further include analyzing a cardiac signal to classify the cardiac signal as either an SVT or a VT using the arrhythmia discrimination algorithm with the programmable parameter (programmed to a second value. The second value can be determined from the identified characteristics of the sensed physiological signal.

20 Claims, 12 Drawing Sheets

(51) Int. Cl.
*A61B 5/00* (2006.01)
*A61N 1/362* (2006.01)
*A61N 1/36* (2006.01)

(56) References Cited

U.S. PATENT DOCUMENTS 7,912,545 B2 3/2011 Li et al.
8,145,301 B2 3/2012 Kim et al.
2010/0211125 A1* 8/2010 Johnson et al. .................. 607/4
2012/0004567 A1 1/2012 Eberle et al.

OTHER PUBLICATIONS

"International Application Serial No. PCT/US2013/070564, Written Opinion mailed Mar. 3, 2014", 4 pgs.

* cited by examiner

METHOD AND SYSTEM FOR ARRHYTHMIA DISCRIMINATION

CLAIM OF PRIORITY

This application claims the benefit of priority under 35 U.S.C. §119(e) of U.S. Provisional Patent Application Ser. No. 61/731,163, filed on Nov. 29, 2012, which is herein incorporated by reference in its entirety.

TECHNICAL FIELD

This document relates generally to cardiac rhythm management systems and more particularly, but not by way of limitation, to a method and system for discriminating a ventricular arrhythmia in a cardiac rhythm management system.

BACKGROUND

The sinoatrial (SA) node controls regular and synchronized contractions among cardiac muscles in the heart. The SA node is a group of specialized cells located in the upper right atrium of the heart that functions as the normal pacemaker of the heart, generating electrical pulses that propagate through an electrical conduction system to various regions of the heart to facilitate the pumping function of the chambers of the heart. Typically, a healthy heart beats at a frequency of 60-100 beats per minute. The heart is in a normal sinus rhythm when the SA node paces the heart normally. The heart is arrhythmic if the heart's electrical activity becomes uncoordinated or irregular.

An arrhythmia involving a slow heart rhythm may be classified as bradycardia, and an arrhythmia involving a fast heart rhythm may be classified as tachycardia. Tachycardia can have its origin in either the atria or the ventricles. Cardiac rhythm management (CRM) systems may be used to treat the arrhythmic conditions of the heart. CRM systems can be configured to discriminate among different types of arrhythmias including supraventricular tachycardia (SVT), ventricular tachyarrhythmia (VT) and ventricular fibrillation (YF), and deliver antiarrhythmic therapy to the heart to interrupt the arrhythmia.

According to a known technique for classifying arrhythmias, a physician programs a programmable parameter of a CRM system to an initial value. The CRM system generally continues to deliver therapies based on the initial value without any intervention of the physician typically until the patient visits the physician during a device checkup. If the initially programmed value of the programmable parameter is not suitable for the patient, the CRM system can erroneously detect or classify cardiac events. For example, the CRM system may detect an arrhythmic episode, misclassify the arrhythmic episode as VT instead of SVT, and incorrectly deliver a therapy for the detected VT. Similarly, for example, the CRM system may detect an arrhythmic episode, misclassify the arrhythmic episode as SVT instead of VT, and incorrectly withheld a therapy for the detected SVT.

SUMMARY

In an example of a method of discriminating tachyarrhythmia, the method may include implementing an arrhythmia discrimination algorithm to discriminate between supraventricular tachycardia (SVT) and ventricular tachycardia (VT) using at least a programmable parameter programmed to a first value. An SVT event may be analyzed. Analyzing the SVT event may include sensing a physiological signal during the SVT event and identifying characteristics of the sensed physiological signal. A second value may be determined from the identified characteristics of the sensed physiological signal. A cardiac signal may be analyzed to classify the cardiac signal as either an SVT or a VT using the arrhythmia discrimination algorithm with the programmable parameter programmed to the second value.

In an example of a system of discriminating arrhythmia, an arrhythmia discriminator may be configured to implement an arrhythmia discrimination algorithm to discriminate between ventricular tachycardia (VT) and supraventricular tachycardia (SVT) using at least a programmable parameter programmed to a first value. An SVT event analyzer may be configured to sense a physiological signal during the SVT event and identify characteristics of the sensed physiological signal. A controller may be configured to determine a second value for the programmable parameter based on identified characteristics of the sensed physiological signal, program the programmable parameter to the second value, and classify a cardiac signal as either an SVT or a VT using the arrhythmia discriminator with the programmable parameter programmed to the second value.

This Summary is an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE. DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
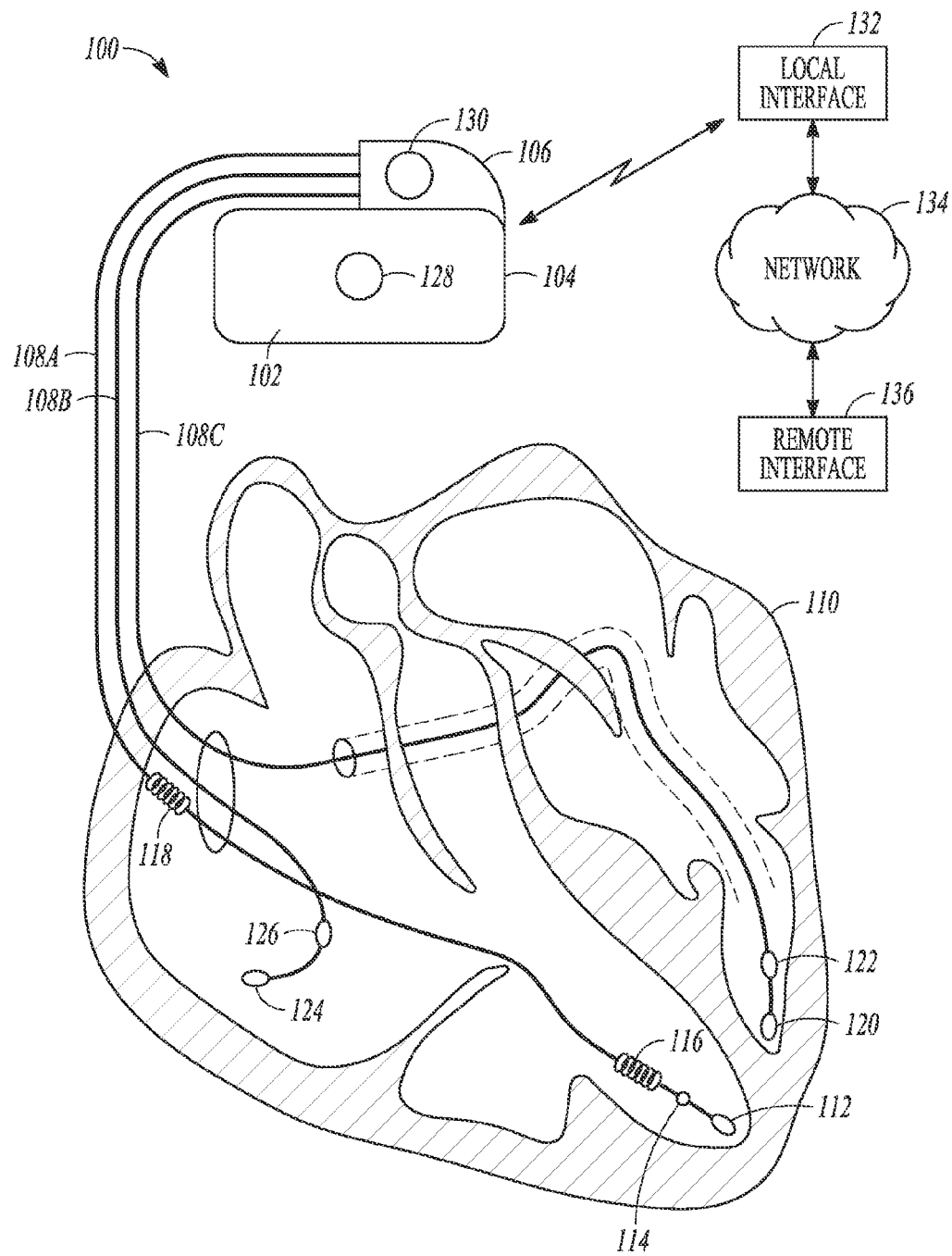
FIG. 1 illustrates, by way of example, an embodiment of a CRM system.

FIG. 1 illustrates, by way of example, an embodiment of a CRM system 100 and an environment in which the CRM system 100 can be used. The illustrated CRM system 100 includes an IMD 102 that can include a hermetically-sealed housing 104 and a header 106 extending from the housing 104. The header 106 can include one or more receptacles for receiving proximal ends of one or more leads such as a lead 108A, a lead 108B, and a lead 108C (collectively referred to herein as leads 108). The distal ends of the leads 108 can include one or more electrical contacts called "electrodes" for use in providing pacing energy, defibrillation energy, or both, to the heart 110. The leads 108 and electrodes can be used to sense electrical activity of the heart 110, including electrical activity related to contractions of the atria or ventricles.

In an example, the lead 108A is an intravascular right ventricle (RV) lead that can extend from a superior vena cava (SVC) into a right atrium (RA), and then into the RV. The lead 108A can include an RV tip electrode 112, a slightly more proximal RV ring electrode 114, a still slightly more proximal RV shock coil electrode 1116, and an even more proximal RA or SVC shock coil electrode 118. In an example, the lead 108B is an intravascular coronary sinus (CS)/left ventricle (LV) lead that can extend from the SVC into the RA through the CS into the coronary vasculature, such as near a portion of the LV. In an example, the CS/LV lead 108B can include a distal electrode 120 and a proximal electrode 122 through which electro-stimulation energies can be delivered or intrinsic electrical heart signals can be sensed. In an example, the lead 108C is an intravascular RA lead 108C that can extend from the SVC into the RA, and can include a distal electrode 124 and a proximal electrode 126. In an example, other electrodes (e.g., a housing electrode 128 on the housing 104, a header electrode 130 on the header 106, an epicardial electrode, a subcutaneous electrode located away from the heart, or an electrode located elsewhere) or leads can be used to provide stimulations to the heart 110 or sense the electrical activity of the heart 110.

Other forms of electrodes include meshes and patches which can be applied to the portions of the heart 110 or which can be implanted in other areas of the body to help "steer" electrical currents produced by the IMD 102. The present methods and systems can work in a variety of configurations and with a variety of electrodes. In an example, the different implantable electrode configurations can include various combinations of sensing and stimulating pairs. For example, one electrode configuration (RA-Can) can be set up by sending a stimulating current between RA-ring electrode and the can housing 104 and sensing the resulting voltage between RA-tip electrode and the can housing 104. The other configurations can include but are not limited to RV-Can (configuration utilizing electrodes on the RV lead and active pectoral can for stimulation and sensing), LV-Can (configuration utilizing electrodes on the UV lead and active pectoral can for stimulation and sensing), RA-LV-Can (configuration utilizing electrodes on the Right Atrial lead, LV lead and active can for stimulation and sensing), RV-LV (configuration utilizing electrodes on Right Ventricular lead and Left Ventricular lead for sensing and stimulating), and the like. The electrodes typically deliver cardioversion, defibrillation, pacing, or resynchronization therapy, or combinations thereof to at least one chamber of the heart 110.

Examples of the IMD 102 can include, without limitation, a pacer, a defibrillator, a cardiac resynchronization therapy (CRT) device, or a combination of such devices. The IMD 102 can communicate, wirelessly or through a wired connection. For example, the IMD 102 can communicate using a tether uni-directionally or bi-directionally with an external local interface 132 such as an IMD programmer, repeater, handheld device, and the like. The local interface 132 can be configured to communicate via a wired or wireless computer or communication network 134 to a remote interface 136, such as a remote computer, a server, and the like.

In an example, the IMD 102 can include a neural stimulator to deliver neural stimulations to one or more neural targets. As discussed above, the CRM system 100 can be configured to use the local interface 132 such as to program the IMD 102 to deliver neural stimulation to the patient. For example, the local interface 132 can communicate wirelessly with the IMD 102 to deliver stimulating energy to one or more nerves of the body. In some examples, the CRM system 100 can wirelessly supply operating energy to a neural stimulation IMD such as the IMD 102.

The present systems or methods can be configured to enable diagnosis and management of cardiac arrhythmias and/or congestive heart failure ("CHF" or "heart failure") using one or more programmable parameters. Further, the systems or methods disclosed herein can enable the physician to identify factors related to change(s) in conductivity characteristic(s) of the patient and accordingly, can recommend a threshold value for the programmable parameter. The physician can confirm the recommended threshold value and the system can be configured to discriminate the cardiac arrhythmias as VT or SVT using the recommended threshold value of the programmable parameter.

Figure 2:
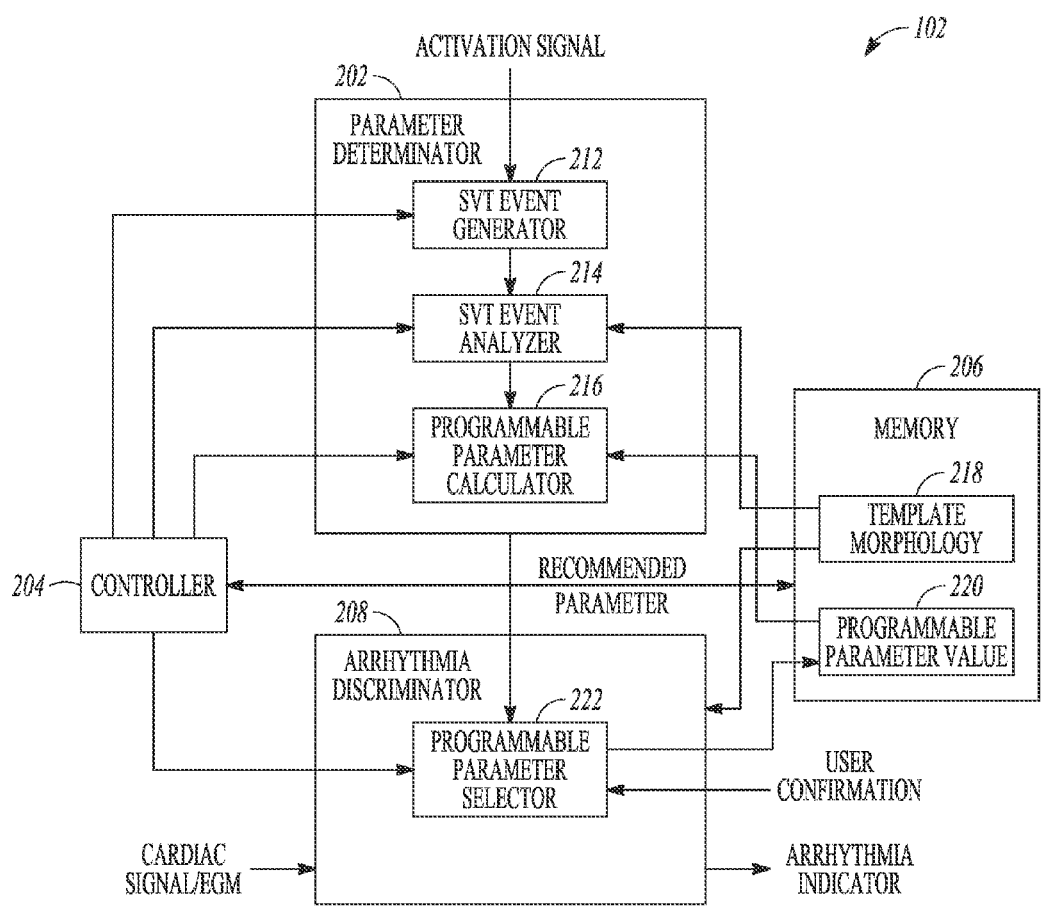
FIG. 2 illustrates, by way of example, an embodiment of an implantable medical device (IMD) configured to discriminate between or among arrhythmias.

FIG. 2 illustrates, by way of example, an embodiment of the IMD 102. The IMD 102 can be programmed for and operated based on several programmable parameters to discriminate between or among arrhythmias. For example, the IMD 102 can be configured to determine if the arrhythmia is an atrial arrhythmia, a ventricular arrhythmia. In an example, the IMD 102 can be configured to determine if the arrhythmia is bradycardia or tachycardia. In an example, the IMD 102 can be configured to discriminate between ventricular tachycardia (VT) and supraventricular tachycardia (SVT). In an example, the several programmable parameters can indicate atrial or ventricular rate threshold values, fibrillation threshold values, correlation threshold values, stability threshold values or other sensing threshold values. The IMD 102 can be configured to use the threshold values of one or more programmable parameters and detect the presence of a particular arrhythmia using the one or more electrode configurations. Accordingly, the IMD 102 can be programmed to initiate or provide therapy to the patient in accordance with the detected arrhythmia.

In an example, the programmable parameter(s) of the IMD 102 are programmed to initial threshold value(s). For example, a physician can manually provide the initial threshold value of the programmable parameter. In an example, the physician can select a particular mode (e.g., a tachy mode) of operation of the IMD 102 and the initial threshold value can be automatically set based on the selection of the mode of operation. In an operating environment, the IMD 102 can be configured to sense cardiac signals and thereby discriminate the cardiac signals as VT or SVT using the initial value of the programmable parameter.

In an example, the programmable parameter can be indicative of morphological similarities between a cardiac depolarization morphology and a template morphology. The IMD 102 can be configured to set an initial morphology similarity threshold value for a programmable parameter. The IMD 102 can be configured to sense the cardiac signal and determine the depolarization morphology of the cardiac signal. Thereafter, the IMD 102 can be configured to compute the similarity between the determined cardiac depolarization morphology and the template morphology. In an example, an FCC value can be used to determine or assess the extent of similarity between the two morphologies. Accordingly, the IMD 102 can be configured to discriminate the cardiac signal as VT or SVT using the computed FCC value and the initial morphology similarity threshold value.

In an example, the programmable parameter can be a stability analysis parameter for use to provide a stability threshold value used to distinguish unstable ventricular rhythms from stable ventricular rhythms. The IMD 102 can be configured to set an initial threshold value for the stability analysis parameter for use to indicate a degree of variability of the tachycardia R-R intervals. The IMD 102 can be configured to measure a degree of variability of R-R intervals of the cardiac signal and compare the measured value with the threshold value of the stability parameter. The IMD 102 can be configured to declare the VT rhythm as unstable if the measured degree of variability is greater than the threshold value of programmable parameter. Otherwise, the IMD 102 can be configured to declare the VT rhythm as stable.

In an example, the IMD 102 includes a parameter determinator 202, a controller 204, a memory 206 and an arrhythmia discriminator 208. The parameter determinator 202 can include an SVT event generator 212, an SVT event analyzer 214, and a programmable parameter calculator 216. The memory 206 can be configured to store template morphology 218 and a programmable parameter value 220 for the respective one or more programmable parameters. The arrhythmia discriminator 208 can include a programmable parameter selector 222. The programmable parameter selector 222 may be used to select the second threshold value of the programmable parameter.

In an example, the controller 204 can be configured to determine the second value of the programmable parameter using the parameter determinator 202 and the template morphology 218. The SVT event generator 212 of the parameter determinator 202 can be configured to generate an SVT event upon receiving an activation signal. A physiological signal can be sensed and thereafter, analyzed by the SVT event analyzer 214 to identify characteristics of the physiological signal using the template morphology 218. The programmable parameter calculator 216 can be configured to compute the second value of the programmable parameter using the identified characteristics of the physiological signal and the programmable parameter value 220.

In an example, the controller 204 can be configured to provide instructions to the SVT event generator 212 to induce the SVT event. The induction of the SVT event can include delivering a programmed cardiac stimulation sequence to the heart 110. Alternatively, the induction of the SVT event can include delivering a programmed neural stimulation sequence to an autonomic neural target. In another example, the controller 204 can be configured to simulate the SVT event using the SVT event generator 212. The simulating of the SVT event can include delivering a programmed cardiac pacing sequence to the heart 110. In yet another example, the controller 204 can be configured to record an intrinsic, spontaneously occurred SVT event.

In response to the induced, simulated or intrinsic SVT event, one or more physiological signals are sensed. The one or more physiological signals can be a cardiac electrocardiogram (ECG) signal, intracardiac electrogram (EGM) signal, impedance signal, pressure signal, cardiac contraction pattern, or any other signal. In an example, the controller 204 can be configured to store the data associated with the physiological signal in the memory 206 or send the data associated with the physiological signal to the SVT event analyzer 214. In an example, the controller 204 can be configured to extract this data associated with the physiological signals from the memory 206 as and when required. The extracted data can indicate the information associated with earlier intrinsic or extrinsic (i.e., generated by the SVT event generator 212) SVT events. In an example, the controller 204 can be configured to determine the template morphology 218 for a specified type of rhythm selected from a group of rhythms including but is not limited to a normal sinus rhythm (NSR), an SVT rhythm and a VT rhythm.

In an example, the SVT event analyzer 214 can be configured to sense the physiological signal of the SVT event and identify characteristics of the sensed physiological signal. The characteristics of the physiological signal may include an electrocardiograph (ECG) or electrocardiogram (EGM) pattern, heart rate, stability, heart rate variability, atrioventricular conduction pattern, morphological similarities of the physiological signal with the template morphology, or other characteristics. For example, the SVT event analyzer 214 can identify one or more of these characteristics. The controller 204 can be configured to interact with the programmable parameter calculator 216 to compute the second value of the programmable parameter using the identified characteristic(s) of the physiological signal and the programmable parameter value 220. In an example, the programmable parameter calculator 216 can be configured to implement one or more algorithms to update the value of the programmable parameter from the initial programmable parameter value 220 to the second value as determined by the one or more algorithms.

In an example, the arrhythmia discriminator 208 can be configured to implement an arrhythmia discrimination algorithm to discriminate between ventricular tachycardia (VT) and supraventricular tachycardia (SVT) using at least a programmable parameter programmed to a predetermined value. In an example, the predetermined value can be the initial programmed value for the programmable parameter. In another example, the initial programmed value can be updated to a different value such as the second value as discussed above. The second value can be displayed to the physician and thereby the physician can confirm the selection of the second value for the programmable parameter. In an example, the arrhythmia discriminator 208 can be configured to discriminate the cardiac signal using the most recently updated value of the programmable parameter. In an example, the controller 204 can be configured to provide instructions to the arrhythmia discriminator 208 to extract a plurality of cardiac signal features from the cardiac signal, retrieve a plurality of template features stored in the memory 206, and classify the cardiac signal as either an SVT or a VT using a measure of correlation between the extracted cardiac signal features and the template features.

Figure 3:
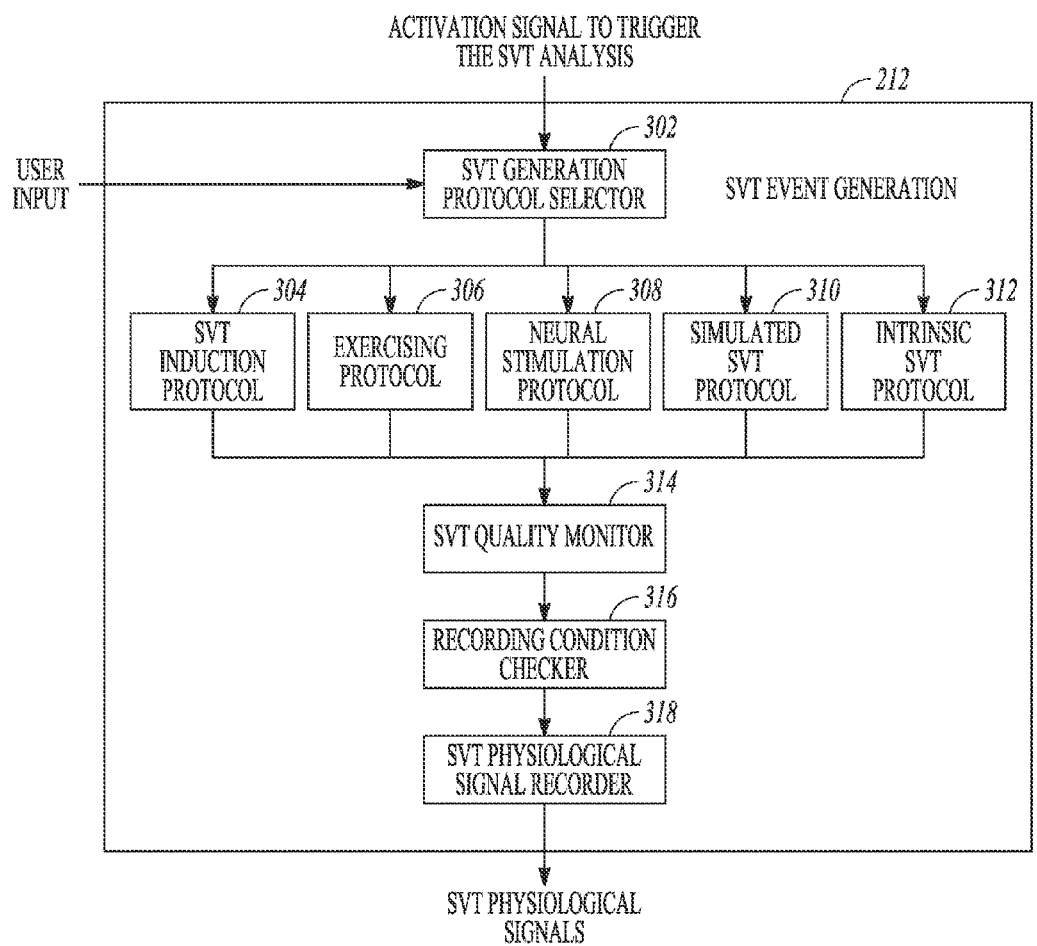
FIG. 3 illustrates, by way of example, an embodiment of an SVT event generator configured to generate the SVT event.

FIG. 3 illustrates, by way of example, an embodiment of an SVT event generator 212 configured to generate the SVT event. On detection of an activation signal such as to trigger the SVT analysis, the SVT event generator 212 can be configured to activate an SVT generation protocol selector 302, providing an interface to the physician to select an option for generating the SVT event from a plurality of SVT event generator protocols. In an example, the physician can provide an input for selecting at least one protocol from the SVT event generation protocols. The protocols available for selection can include at least some of the following protocols: an SVT induction protocol 304, an exercising protocol 306, a neural stimulation protocol 308, a simulated SVT protocol 310, an intrinsic SVT retriever 312, and other event generator protocols. The plurality of SVT event generator protocols can involve various mechanisms for generating the SVT events within the heart 110 of the patient.

In an example, the SVT induction protocol 304 can include programmable or selectable settings for the SVT event generator 212 such as to deliver a short sequence of programmable electrical myocardial stimulation to induce a sustained SVT event. In another embodiment, the SVT event can be generated using the exercising protocol 306 that includes instructions to generate the SVT event through an exercise. The patient's heart rate can be elevated naturally under controlled conditions, using, for example, a treadmill on which the patient exercises. In accordance with the neural stimulation protocol 308, the SVT event generator 212 can be configured to program a neural stimulation sequence with specified values for stimulation parameters and deliver the programmed neural stimulation sequence to a neural target. The stimulation parameters can be defined by at least one of a duration, a pulse width, a frequency, or amplitude of the stimulated pulse.

The simulated SVT protocol 310 can include settings to generate the SVT event using a simulated pacing sequence. In accordance with the simulated SVT protocol 310, the SVT event generator 212 can be configured to program the cardiac pacing sequence with a specified cardiac pacing mode and a pacing rate higher than a normal resting heart rate of the patient and deliver the cardiac pacing sequence to the heart 110. In an example, the SVT generation protocol selector 302 can be configured to select the intrinsic SVT retriever 312 that can extract the data associated with the past SVT events stored in the memory 206.

The SVT event generator 212 can be configured to monitor the quality of the SVT signal (i.e., the physiological signal) using an SVT quality monitor 314. The process of quality monitoring can ensure a reliable signal quality for the selected sensing configurations. The SVT event generator 212 can be configured to verify one or more recording conditions using the recording condition checker 316. The SVT event generator 212 can be configured to record the physiological signal using an SVT physiological signal recorder 318 when one or more recording conditions are met. In an example, the SVT physiological signal recorder 318 can be configured to record an electrocardiogram of the SVT event. Accordingly, the SVT event generator 212 can be configured to provide the recorded physiological signal to the SVT event analyzer 214 for further analysis.

Figure 4:
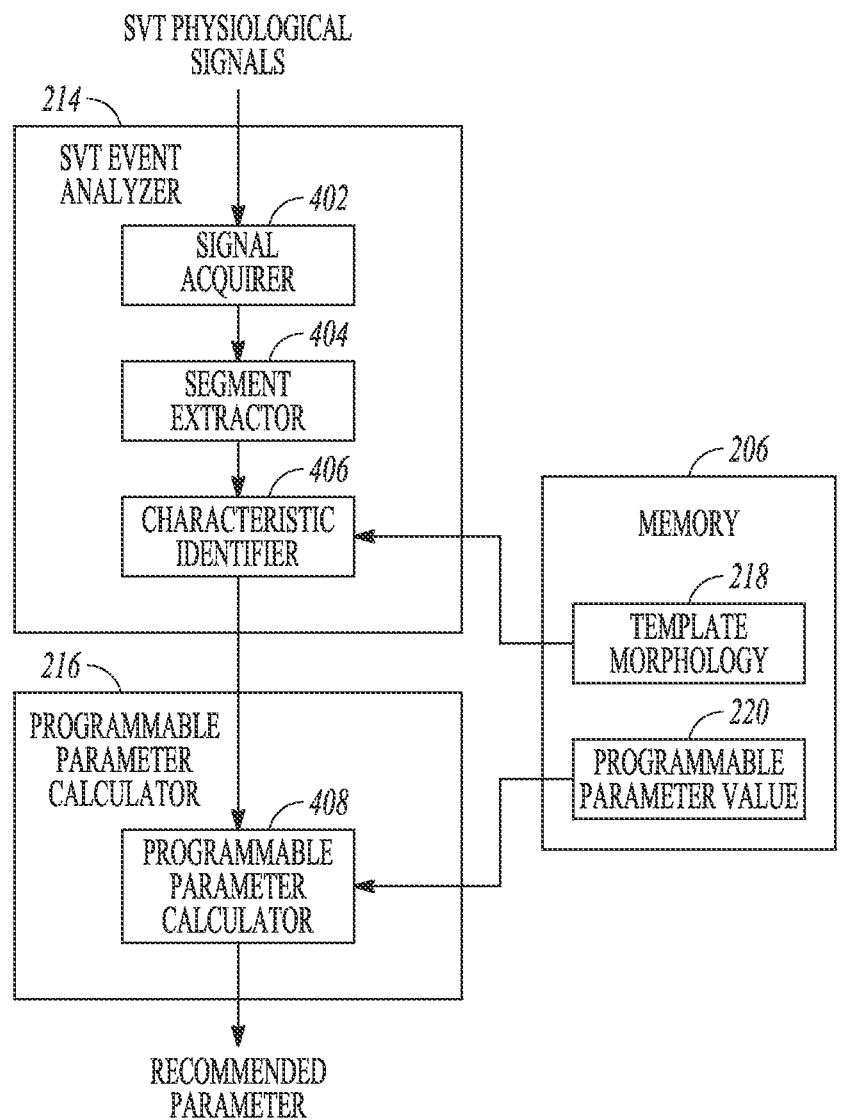
FIG. 4 illustrates, by way of example, an embodiment of an SVT event analyzer configured to identify characteristics of a physiological signal for an SVT.

FIG. 4 illustrates, by way of example, and embodiment of the SVT event analyzer 214 configured to identify characteristics of the physiological signal. The SVT event analyzer 214 can be configured to include a signal acquirer 402, a segment extractor 404, and a characteristic identifier 406. The signal acquirer 402 can be configured to acquire the physiological signal so that the SVT event analyzer 214 can analyze the physiological signal to provide analyzed data to the programmable parameter calculator 216. In an example, the SVT event analyzer 214 can acquire the physiological signal directly from the SVT event generator 212 or retrieve the physiological signal from the memory 206.

The segment extractor 404 can be configured to extract a plurality of physiological signal segments from the physiological signal and the characteristic identifier 406 can be configured to identify characteristics of the segments of the physiological signal. In an example, the characteristic identifier 406 can be configured to determine the characteristics of the physiological signal by computing a morphological similarity metric between the plurality of physiological signal segments and the template morphology 218. In an example, the morphology similarity can be defined by the feature correlation coefficient (FCC) value. The FCC value provides a measure of the similarity of a particular feature from the physiological signal to the same feature in the template morphology 218. Values closer to "1" provides an indication of more similarity than values further away from "1". The template morphology 218 can be determined from a specified type of rhythm that can be selected from a group of rhythms including but is not limited to a normal sinus rhythm (NSR), an SVT rhythm, a VT rhythm, and others.

The programmable parameter calculator 216 can be configured to use the identified characteristics of the physiological signal to determine the second value of the programmable parameter using the programmable parameter comparator 408. In an example, the programmable parameter comparator 408 can be configured to compare the identified FCC value obtained from the characteristics of the physiological signal with the programmable parameter value 218 using one or more methods as described later in this document. Accordingly, the programmable parameter comparator 408 can recommend a new FCC value for the programmable parameter.

Figure 5:
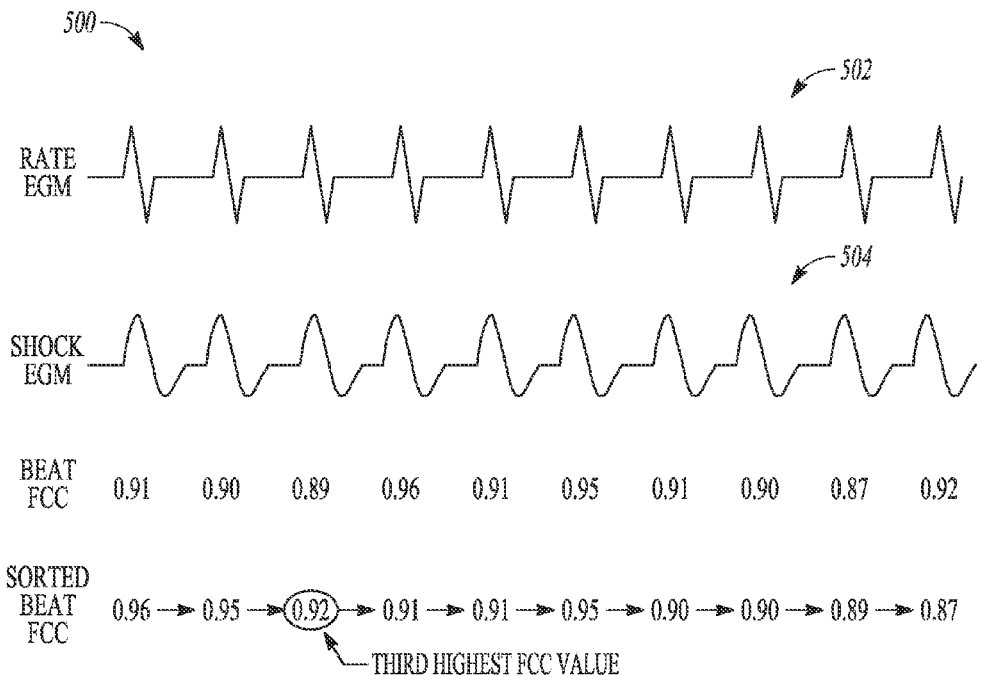
FIG. 5 illustrates, by way of example, an embodiment of a process for calculating a Feature Correlation Coefficient (FCC) value for use in recommending a second value for the programmable parameter.

FIG. 5 illustrates, by way of example, an embodiment of a process for calculating an FCC value for use in recommending the second value for the programmable parameter. Referring to FIG. 4 and FIG. 5, the signal acquirer 402 can acquire a "rate electrogram (EGM)" 502 (RVtip to RVring or RVtip to RA/coil EGM, which is the near-field signal used for ventricular rate sensing) and a "shock EGM" 504 (RA/coil to can housing EGM, which is the far-field signal, and the vector may also be used for delivering defibrillation shock) from the sensed physiological signal generated during the SVT event. The segment extractor 404 can be configured to use the rate EGM 502 and/or the shock EGM 504 to extract data for each beat associated with the physiological signal. Further, the characteristic identifier 406 can be configured to compute the FCC value of each beat of the physiological signal using the template morphology 218. As illustrated in FIG. 5, for an example, the characteristic identifier 406 determines the FCC values for 10 beats of the shock EGM 504. The FCC value can indicate the measure of correlation between the shock EGM 504 and the template morphology 218.

The programmable parameter calculator 216 can be configured to utilize these FCC values with the programmable parameter comparator 408 while implementing one or more methods (as discussed later in this document) to compute an FCC value that can be recommended for the programmable parameter. In one embodiment, a detected arrhythmia is classified as SVT if at least M out of N beats have FCC values that are greater than the FCC threshold value. In this example, a detected arrhythmia is classified as SVT if at least three out of ten beats have FCC values that are greater than or equal to the FCC threshold. The programmable parameter calculator 216 determines the recommended value for the FCC threshold to be a number equal to or less than the third highest FCC value (0.92) among the FCC values of the ten beats, so that the FCC values of at least three out of the ten beats are greater than the recommended FCC threshold value; thereby ensuring that the arrhythmia classification algorithm with the recommended FCC threshold value correctly classifies this SVT rhythm.

Figure 6:
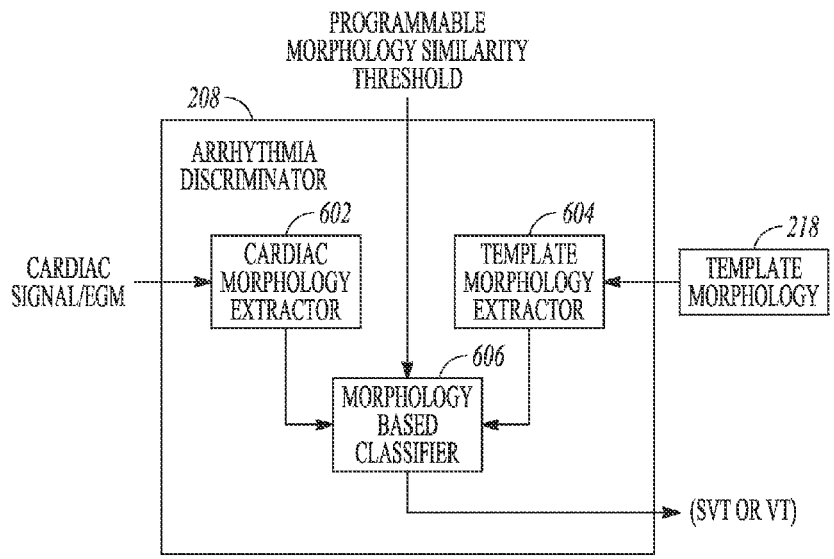
FIG. 6 illustrates, by way of example, an embodiment of an arrhythmia discriminator for discriminating VT and SVT.

FIG. 6 illustrates, by way of example, an embodiment of the arrhythmia discriminator 208 for discriminating the cardiac signal as VT or SVT. Although FIG. 6 indicates an implementation of the morphology-based classifier for arrhythmia discrimination, other features such as stability and/or ventricular rates can be employed to discriminate the arrhythmia. The arrhythmia discriminator 208 can be configured to include a cardiac morphology extractor 602, template morphology extractor 604 and a morphology based classifier 606.

In an example, the controller 204 can be configured to use the cardiac morphology extractor 602 to determine a cardiac depolarization morphology from the cardiac signal and the template morphology extractor 604 to determine the template morphology feature from a specified type of rhythm that can be selected from a group of rhythms including but not limited to a normal sinus rhythm (NSR), an SVT rhythm, a VT rhythm, and others. In an example, the morphology based classifier 606 can be configured to generate a correlation metric between the cardiac depolarization signal and the template morphology 218. The morphology based classifier 606 can be configured to use the programmable morphology similarity threshold value as a reference value and accordingly, classify the cardiac signal as VT or SVT. For example, if the FCC value determined for the cardiac signal is greater than or equal to the reference FCC value, the morphology based classifier 606 can classify the cardiac signal as an SVT beat. If a significant number of beats are classified as SVT beats (e.g., at least 3 out of 10 beats are SVT beats), morphology based classifier 606 classifies the rhythm as an SVT rhythm, and a VT therapy can be inhibited. If the FCC value of the cardiac signal is less than the reference FCC value, the morphology based classifier 606 can classify the cardiac signal as a VT beat. If a significant number of beats are classified as VT beats (e.g., at least 8 out of 10 beats are VT beats), the morphology based classifier 606 classifies the rhythm as a VT rhythm; and accordingly, a VT therapy can be initiated.

Figure 7:
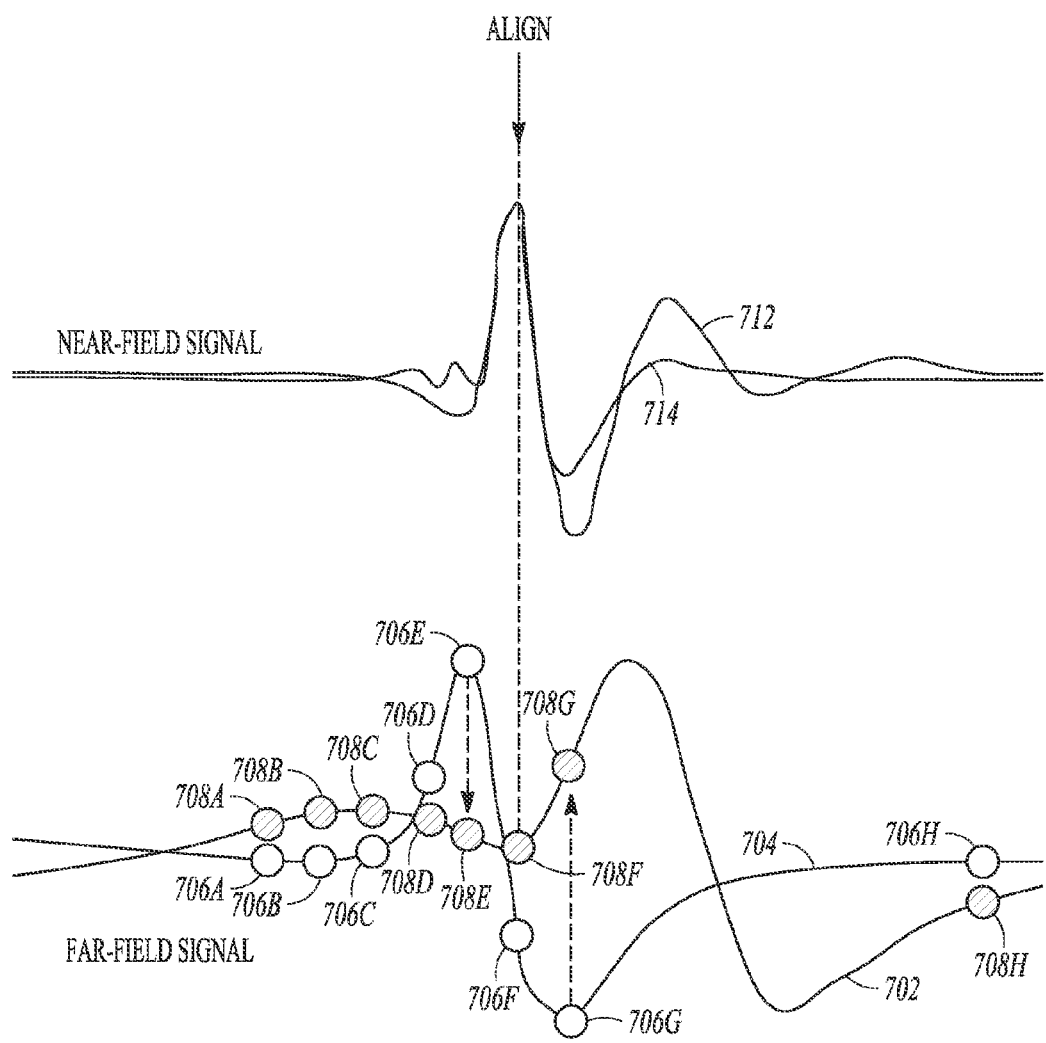
FIG. 7 illustrates, by way of example, an embodiment for comparing a cardiac signal to a template.

FIG. 7 illustrates, by way of example, an embodiment for comparing a received cardiac signal 702 to a template 704 of the template morphology 218. In this example, template 704 is an NSR template created from a far-field NSR signal, and the cardiac signal 702 is a beat (i.e., cardiac depolarization) obtained from a far-field arrhythmia signal, in an example, the far-field signal can be the "shock EGM" sensed using RVcoil electrode and can housing. As illustrated, the received cardiac signal 702 and the template 704 can be aligned by an alignment feature such as an R-wave peak of the respective near-field signal 712 of the cardiac signal and the near-field signal 714 of the template. In an example, the near-field signal is the "rate EGM" sensed using RVtip and RVring (or RVcoil) electrodes.

In an example, the template 704 can include a collection of eight morphology-defining features 706A-H and the template 704 can include the times and amplitudes of each of the eight features 706A-H for comparison to the cardiac signal 702 such that the cardiac signal 702 can be discriminated as the VT or SVT. The cardiac signal 702 can be sampled at same time interval (relative to the alignment feature) as the features 706A-H in the template 704, yielding comparison features 708A-H. Further, the arrhythmia discriminator 208 can be configured to compute the FCC value using the amplitude ($x_i$) of each of the template features 706A-H and the amplitude ($y_i$) of the cardiac signal 708A-H relative to the alignment feature, as illustrated by the following equation:

$$FCC = \frac{\left[8\sum_{i=1}^{8} x_i y_i - \left[\sum_{i=1}^{8} x_i\right]\left[\sum_{i=1}^{8} y_i\right]\right]^2}{\left[8\sum_{i=1}^{8} x_i^2 - \left[\sum_{i=1}^{8} x_i\right]^2\right]\left[8\sum_{i=1}^{8} y_i^2 - \left[\sum_{i=1}^{8} y_i\right]^2\right]}$$

In an example, the FCC computed in accordance with the above equation can be compared to the programmable morphology similarity threshold value such as to determine whether the cardiac signal 702 is correlated to the template 704.

Figure 8:
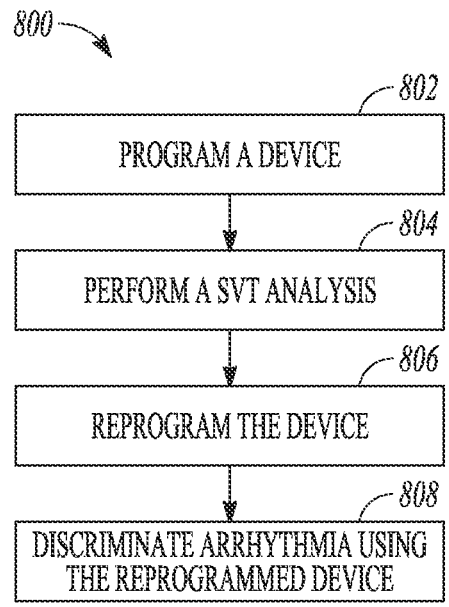
FIG. 8 illustrates, by way of example, an embodiment of a method for discriminating the arrhythmia.

FIG. 8 illustrates, by way of example, an embodiment for comparing a method 800 for discriminating the arrhythmia. At 802, a device such as the IMD 102 is programmed initially such as to implement an arrhythmia discrimination algorithm that can discriminate between supraventricular tachycardia (SVT) and ventricular tachycardia (VT) using one or more programmable parameters. In an example, at least one programmable parameter can be programmed to a first value. The IMD 102 can use the first value of the programmable parameter such as to facilitate the discrimination between the VT and the SVT.

At 804, an SVT analysis is performed. In an example, the SVT analysis can include analyzing an SVT event that can include sensing a physiological signal during the SVT event and identifying characteristics of the sensed physiological signal in an example, the identified characteristics of the physiological signal can include a morphological similarity metric between a plurality of segments of the physiological signal and the template morphology. In an example, the morphological similarity metric can include a measure of correlation between the sensed physiological signal and the template morphology. In an example, the template morphology can be determined from a specified type of rhythm selected from a group of rhythms including at least one of a normal sinus rhythm (NSR), an SVT, and a VT. Further, the SVT analysis can be used to generate a second value for the at least one programmable parameter using the identified characteristics of the sensed physiological signal.

At 806, the IMD 102 can be reprogrammed using the second value. In an example, the second value of the programmable parameter can be more sensitive toward the detection of at least one of the VT or SVT. At 808, arrhythmia is discriminated using the reprogrammed IMD 102. In an example, the IMD 102 can be configured to reprogram the morphology similarity threshold value to the second value and thereby, analyze a cardiac signal to classify the cardiac signal such as SVT or VT using the second value.

Figure 9:
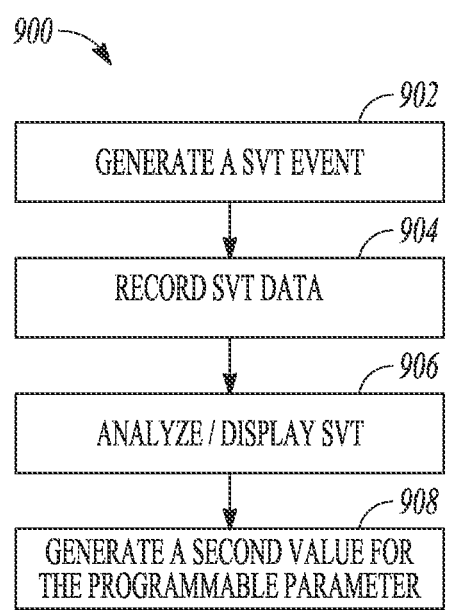
FIG. 9 illustrates, by way of example, an embodiment of a method for generating the second value for the programmable parameter of the MID.

FIG. 9 illustrates, by way of example, and embodiment of a method 900 for generating the second value for the programmable parameter of the IMD 102. At 902, an SVT event is generated. In an example, the method 900 can allow generation of the SVT event either by inducing or simulating the SVT event within the patient's heart 110. In an example, the method of inducing the SVT event can include programming a cardiac stimulation sequence with specified values for stimulation parameters and delivering the programmed cardiac stimulation sequence to the heart 110. The stimulation parameters can include parameters such as duration, pulse width, frequency, amplitude, and others for the one or more stimulation pulses. In an embodiment, the method of inducing the SVT event can include programming a neural stimulation sequence with specified values for stimulation parameters and delivering the programmed neural stimulation sequence to an autonomic neural target. The stimulation parameters can include parameters such as duration, pulse width, frequency, amplitude, and others for the one or more neural stimulation pulses. In an example, the method of simulating the SVT event can include programming a cardiac pacing sequence with a specified cardiac pacing mode and a pacing rate higher than a normal resting heart rate of a patient and delivering the cardiac pacing sequence to the heart 110.

At 904, SVT data is recorded in the memory of the IMD 102. In an example, the method 900 can allow the recording of the SVT data either for a specified duration or for each beat. The data can include information regarding the physiological signal obtained from the electrodes and/or sensors associated with the IMD 102 during the SVT event generation. The data can include information such as count, date, duration and time of the SVT event, electrocardiogram of the physiological signal (e.g., with or without annotated markers), average atrial or ventricle rates and others.

At 906, the SVT data is analyzed such as to perform morphological analysis of the SVT data and the template morphology. In addition to this, the method 900 can display information such as a beat correlation profile based on heart rate, historical data, and so on to the physician. The method 900 can generate the second value for the programmable parameter of the IMD 102 by comparing the FCC values generated during the morphological analysis of the SVT data with the first value of the programmable parameter.

Figure 10:
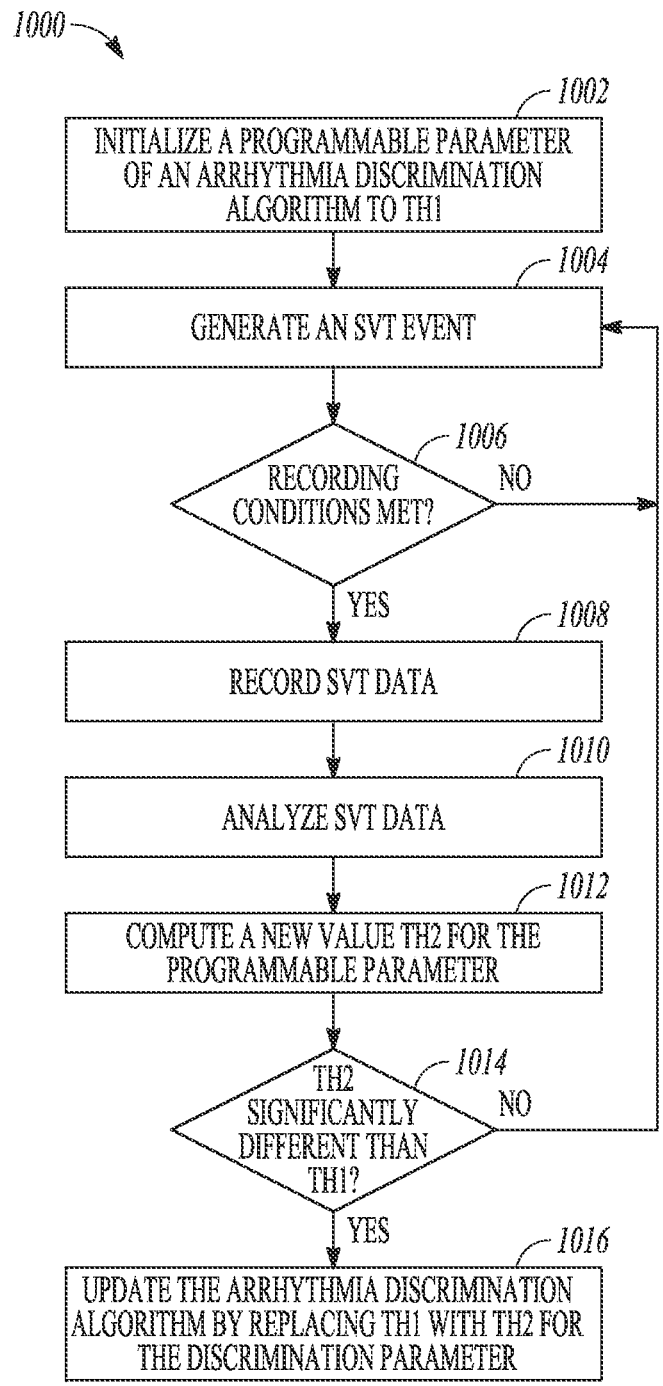
FIG. 10 illustrates, by way of example, an embodiment of a method for updating a threshold value of the programmable parameter using the SVT analysis.

FIG. 10 illustrates, by way of example, an embodiment of a method 1000 for updating a threshold value of the programmable parameter using the SVT analysis. At 1002, a programmable parameter of an arrhythmia discrimination algorithm is initialized to a first threshold value TH1. In an example, the first threshold value of the programmable parameter can indicate a morphology similarity value that can be used to discriminate the cardiac signal as VT or SVT before determining an optimal value (i.e., the second value) for the programmable parameter. At 1004, an SVT event is generated. In an example, the SVT event can be generated in accordance with the step 902 of the method 900. At 1006, a determination can be made as to whether one or more recording conditions for recording the SVT event are met. In an example, the one or more recording conditions can include receiving a confirmation from the physician to initiate the recording of the SVT event, in an example, the one or more recording conditions can include an occurrence of an event such as an occurrence of an atrial tachy response (ATR) episode with slow ventricular response. In an example, the recording can be initiated after a programmed delay. The method 1000 can proceed to 1004 if the recording conditions are not met and at 1004, the SVT event can be generated. The method 1000 proceeds to 1008 if the recording conditions are met, and at 1008, the SVT data is recorded. The SVT data can include a summary of an episode (e.g., atrial rate and ventricular rate), SVT generation protocol, parameters used in the protocol (e.g., pulse width and stimulation frequency), electrocardiograms (EGMs) such as with or without annotated markers, and other information associated with the SVT event.

At 1010, the SVT data is analyzed. In an example, analyzing the SVT event can include sensing the physiological signal during the SVT event, and identifying characteristics of the sensed physiological signal. The identified characteristics can include the morphological similarity metric between a plurality of segments of the physiological signal and the template morphology. The morphological similarity metric can include a measure of correlation between the one or more segments of the physiological signal and the template morphology. At 1012, based on the correlation values, a new threshold value TH2 is computed for the programmable parameter. In an example, the threshold value TH2 can be computed in accordance with the method 1200, as described herein below.

At 1014, a determination is made as to whether the new threshold value TH2 is significantly different from the initial threshold value TH1. The method 1000 can proceed to 1004 if the new threshold value TH2 is not significantly different from the initial threshold value TH1 and at 1004, and another SVT event can be generated. The method 1000 proceeds to 1016 if the threshold value TH2 is significantly different from the initial threshold value TH1 of the programmable parameter and at 1016, an arrhythmia discrimination algorithm is updated by replacing the initial threshold value TH1 of the discrimination programmable parameter with the newly computed threshold value TH2. Accordingly, the IMD 102 can classify the cardiac signal as VT or SVT in accordance with the updated value of discrimination programmable parameter.

Figure 11:
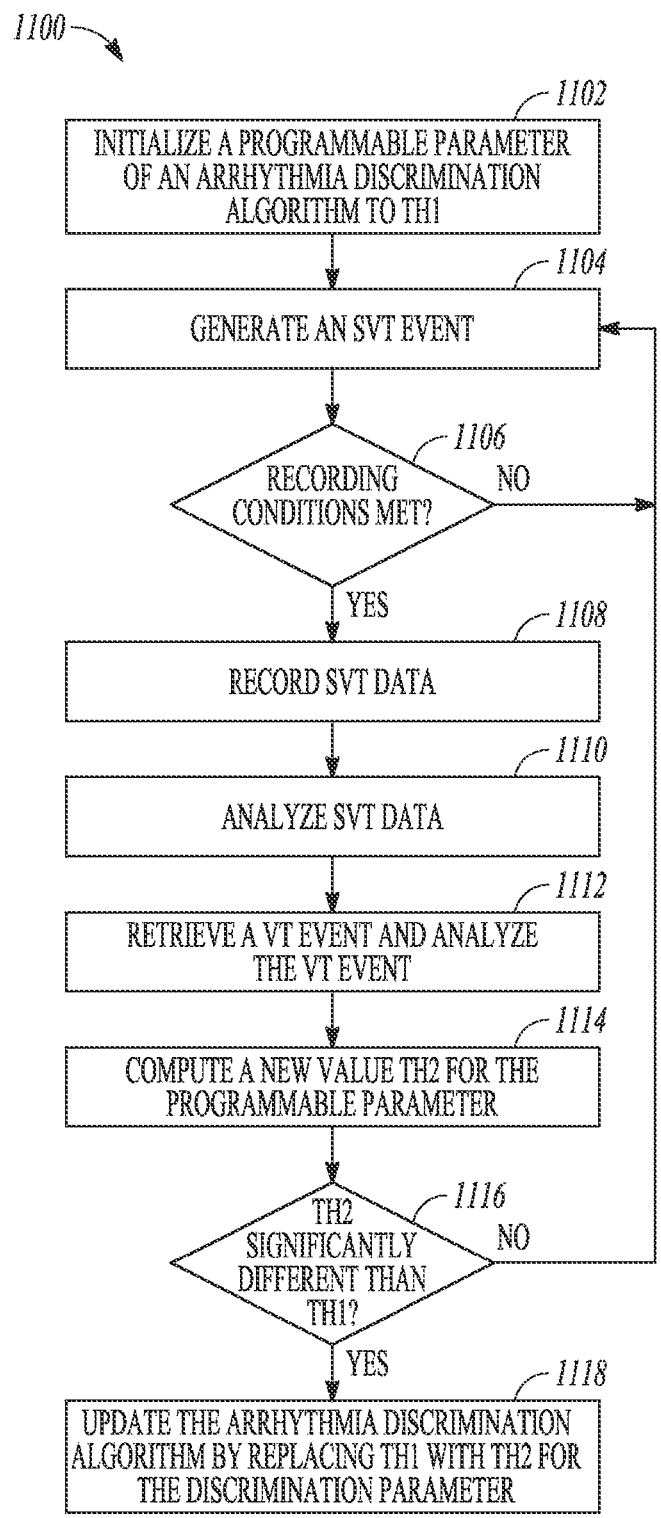
FIG. 11 illustrates, by way of example, an embodiment of a method for updating a threshold value of the programmable parameter using the SVT and the VT analysis.

FIG. 11 illustrates, by way of example, an embodiment of a method 1100 for updating the threshold value of the programmable parameter using the SVT and the VT analysis. At 1102, a discrimination programmable parameter of an arrhythmia discrimination algorithm is initialized to the first threshold value TH1, and at 1104, an SVT event is generated. At 1106, a determination can be made as to whether one or more recording conditions for recording the SVT event are met. The method 1100 can proceed to 1104 if the recording conditions are not met and at 1104, the SVT event can be generated. The method 1100 can proceed to 1108 if the recording conditions are met and at 1108, the SVT data can be recorded. At 1110, the SVT data can be analyzed.

At 1112, a VT event is retrieved and analyzed. In an example, the VT event can be retrieved from the history data stored in the memory 206 of the IMD 102. The memory may store historical data (e.g., EGM associated with these event or episodes) associated with the various events and other episodes that have occurred in the past. The method 1100 can retrieve the data associated with the VT event occurred in the past from the memory 206 of the IMD 102 and thereby analyze the VT data such as to compute correlation values.

At 1114, based on the correlation values of the VT and SVT events, a new threshold value TH2 is computed for the programmable parameter. In an example, the threshold value TH2 can be computed in accordance with the method 1400, as described herein below. At 1116, a determination is made as to whether the new threshold value TH2 is significantly different from the initial threshold value TH1. The method 1100 can proceed to 1104 if the new threshold value TH2 is not significantly different from the initial threshold value TH1 and at 1104, and another SVT event can be generated. The method 1100 can proceed to 1118 if the threshold value TH2 is significantly different from the initial threshold value of the programmable parameter. At 1118, the arrhythmia discrimination algorithm is updated by replacing the initial threshold value TH1 of the discrimination programmable parameter with the new threshold value TH2. Accordingly, the IMD 102 can classify the cardiac signal as VT or SVT in accordance with the updated value of discrimination programmable parameter.

Figure 12:
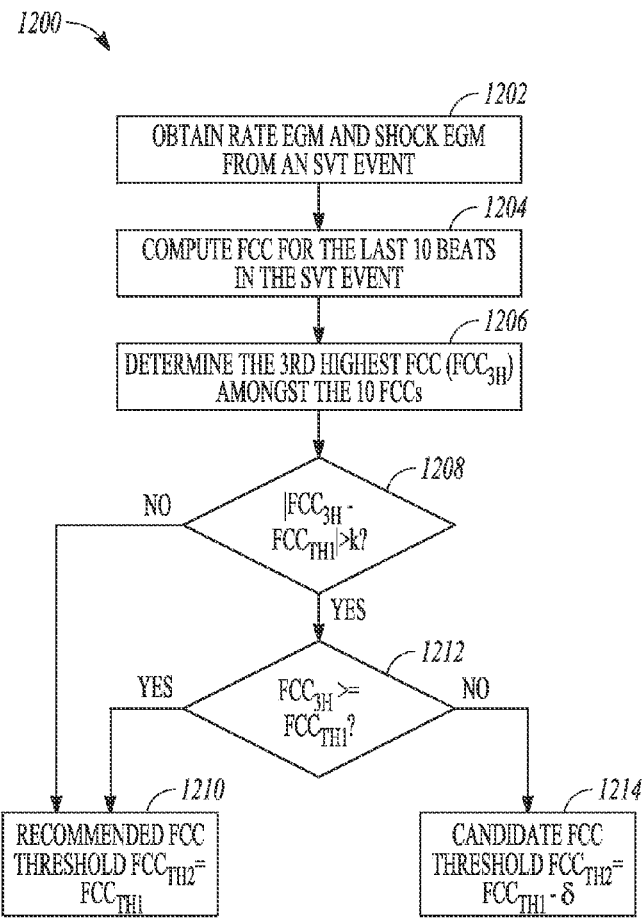
FIG. 12 illustrates, by way of example, an embodiment of a method for computing a threshold value of the programmable parameter using the analysis of the SVT event.
Figure 13:
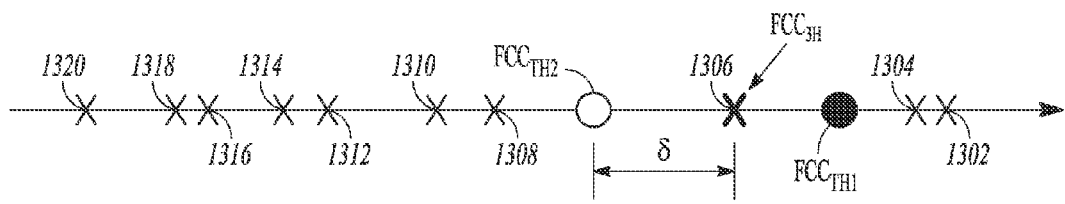
FIG. 13 illustrates, by way of example, an embodiment listing FCC values of a plurality of beats in the physiological signal generated during the SVT event.

Referring to FIG. 12 and FIG. 13, a flow diagram of an example of a method 1200 for computing a threshold value of the discrimination programmable parameter using the SVT event is disclosed. In an example, the method 1200 can include computing the new threshold value $FCC_{TH2}$ for the discrimination programmable parameter as indicated at 1012 of the FIG. 10. At 1202, a rate EGM and a shock EGM are obtained from the SVT event, in an embodiment, the SVT event can be an intrinsic SVT event, an induced SVT event or a simulated SVT event. At 1204, FCC value of each beat for the last ten beats of the SVT event can be computed. At 1206, a third highest FCC value ($FCC_{3H}$) amongst the computed FCC values can be determined. As indicated in the FIG. 13, FCC values of the last ten beats of the SVT event are computed and are shown on a linear scale as FCC values 1302-J320. Further, as an example, the FCC values are shown as arranged in an increasing order in which the FCC value 1302 is the highest value and the FCC value 1320 is the lowest value amongst the computed FCC values. The initial threshold FCC value is shown as $FCC_{TH1}$. The FCC value 1306 is the third highest FCC value ($FCC_{3H}$) amongst the various FCC values.

A decision is made to determine whether the third highest FCC values ($FCC_{3H}$) is greater than the initial threshold value ($FCC_{TH1}$) of the discrimination programmable parameter. In other words, a decision is made to determine an amount of difference between the ($FCC_{3H}$) and ($FCC_{TH1}$). If the third highest FCC value ($FCC_{3H}$) is not significantly different from the initial threshold value ($FCC_{TH1}$), then the method 1200 proceeds to 1210 and the method 1200 can recommend the initial threshold value ($FCC_{TH1}$) as the recommended threshold value for the discrimination programmable parameter. In other words, the initial threshold value ($FCC_{TH1}$) can accurately discriminate the cardiac signal as VT or SVT, and accordingly the IMD 102 can provide the therapy to the patient based on the discrimination determined using the initial threshold value ($FCC_{TH1}$).

If the third highest FCC value ($FCC_{3H}$) is significantly different from the initial threshold value ($FCC_{TH1}$), the method 1200 can proceed to 1212. At 1212, a decision is made to determine as to whether the third highest FCC value ($FCC_{3H}$) is greater than or equal to the initial threshold value ($FCC_{TH1}$) of the programmable parameter. If the third highest FCC value ($FCC_{3H}$) is greater than or equal to the initial threshold value ($FCC_{TH1}$) of the programmable parameter, the method 1200 can proceed to 1210 and the method 1200 recommends the initial threshold value ($FCC_{TH1}$) as the recommended threshold value for the programmable parameter. If the third highest FCC value ($FCC_{3H}$) is smaller than the initial threshold value ($FCC_{TH1}$) of the programmable parameter, the method 1200 can proceed to 1214, and the method 1200 can compute the second threshold value ($FCC_{TH2}$) of the programmable parameter by subtracting a variable delta ($\delta$) from the third highest FCC value ($FCC_{3H}$). In one example, $\delta$ is a programmable number ranging from 0.01 to 0.1. In another example, $\delta$ is a pre-determined positive constant. In an arrhythmia discrimination algorithm that classifies an arrhythmia as SVT if at least three out of ten beats have FCC values that are greater than or equal to the FCC threshold, using the recommended second threshold value $FCC_{TH2}$ can cause the generated SVT to be correctly classified as SVT (because there are three FCC values greater than $FCC_{TH2}$, as illustrated in FIG. 13), while using the initial threshold FCC value ($FCC_{TH1}$) would have caused the generated SVT event to be incorrectly classified as VT (because there are only two FCC values greater than $FCC_{TH1}$).

If the third highest FCC value ($FCC_{3H}$) is significantly greater than the initial threshold value ($FCC_{TH1}$), the method 1200 recommends the initial threshold value ($FCC_{TH1}$) as the recommended threshold value. That is to say, the initial threshold value ($FCC_{TH1}$) is an optimal value for discriminating the cardiac signal as VT or the SVT. In this scenario, the initial threshold value ($FCC_{TH1}$), being an optimal threshold FCC value, can assist in reducing energy requirements of the IMD 102 as the IMD 102 inhibits the VT therapy for the future cardiac signals that have respective FCC correlation values greater than the initial threshold value ($FCC_{TH1}$) of the programmable parameter.

Further, when the third highest FCC value ($FCC_{3H}$) is significantly smaller than the initial threshold value ($FCC_{TH1}$), the method 1200 recommends a second threshold value ($FCC_{TH2}$) that can be significantly smaller than the initial threshold value ($FCC_{TH1}$). In an example, in an operating environment, a physician can program the programmable parameter to an initial FCC value of 0.94. This means that the IMD 102 can discriminate the cardiac signal as the SVT if the FCC value of the cardiac signal is greater than the initial threshold FCC value (i.e., 0.94). Similarly, the IMD 102 can discriminate the cardiac signal as VT if the FCC value of the cardiac signal is less than the initial threshold FCC value (i.e., 0.94). The method 1200, after computing the third highest FCC value of the last ten beats of the SVT event, recommends a second threshold value (for example, 0.90) for the programmable parameter. As a result of the lower second threshold value, the cardiac signal having an FCC value of 0.91 is classified as SVT; and would otherwise have been classified as VT if the initial threshold value had been used. Therefore, by recommending a lower threshold value for the patient, the method 1200 can prevent inappropriate anti-tachyarrhythmia therapy delivered to the SVT episode that has FCC value of 0.91.

Figure 14:
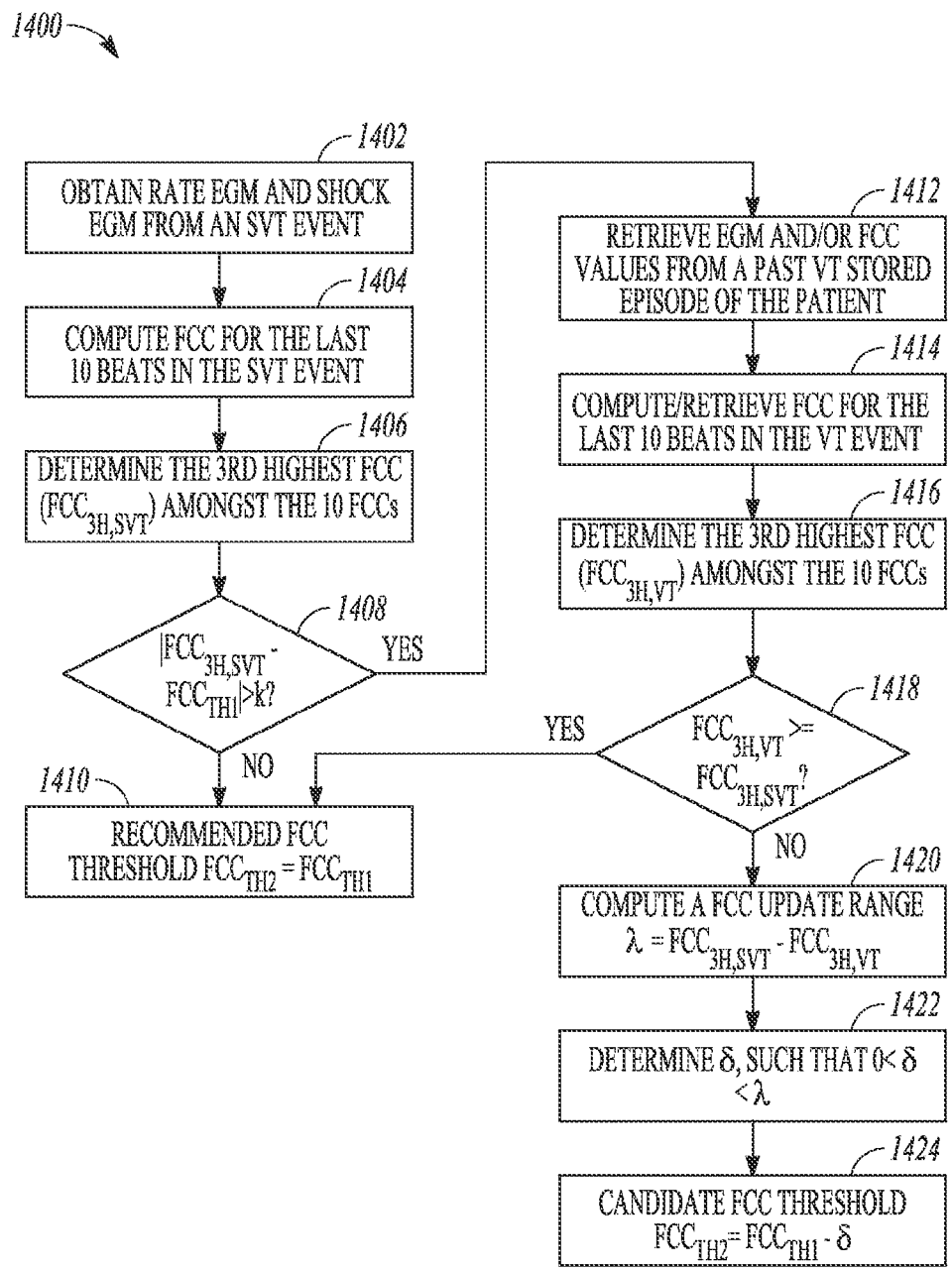
FIG. 14 illustrates, by way of example, an embodiment of a method for computing a threshold value of the programmable parameter using the analysis of the SVT event and the VT event.
Figure 15:
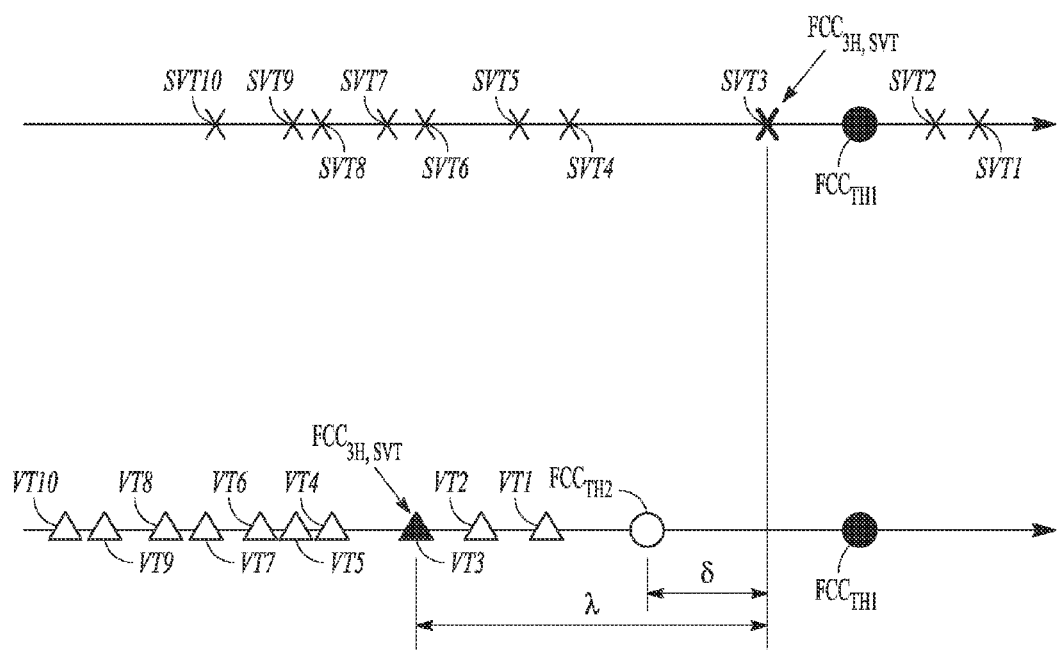
FIG. 15 illustrates, by way of example, an embodiment listing FCC values of a plurality of beats in the physiological signals generated during the SVT event and the VT event.

Referring to FIG. 14 and FIG. 15, a flow diagram of an example of a method 1400 for computing a threshold value of the discrimination programmable parameter using the analysis of an SVT event and a VT event is disclosed. In an example, the method 1400 can compute the new threshold value TH2 for the discrimination programmable parameter as indicated at 1114 of the FIG. 11. At 1402, a rate EGM and a shock EGM is obtained from the SVT event. In an example, the SVT event can be an intrinsic SVT event, an induced SVT event or a simulated SVT event. At 1404, FCC values of each beat for the last ten beats in the SVT event can be computed. At 1406, a third highest FCC value ($FCC_{3H,SVT}$) amongst the computed FCC values of the SVT event can be determined. As indicated in the FIG. 15, FCC values of the last ten beats of the SVT event are computed and are shown on a linear scale as FCC values SVT1-SVT10. The FCC values of the SVT event are shown as arranged in an increasing order in which the FCC value SVT1 has the highest value and the FCC value SVT 10 has the lowest value amongst the computed FCC values for the SVT. As illustrated in the FIG. 15, the FCC value SVT3 has the third highest value ($FCC_{3H,SVT}$) amongst the various FCC values for the SVT event.

On determination of the third highest FCC value ($FCC_{3H,SVT}$), the method 1400 can determine the difference between the selected FCC value ($FCC_{3H,SVT}$) and the initial threshold FCC value ($FCC_{TH1}$) of the discrimination programmable parameter. At 1408, a decision is made as to determine whether the third highest FCC value ($FCC_{3H,SVT}$) is significantly different from the initial threshold value FCC value ($FCC_{TH1}$) of the discrimination programmable parameter. If the third highest FCC value ($FCC_{3H,SVT}$) is not significantly different from the initial threshold FCC value ($FCC_{TH1}$), then the method 1400 can proceed to 1410 and the method 1400 recommends the initial threshold value ($FCC_{TH1}$) for the discrimination programmable parameter as a recommended second threshold value ($FCC_{TH2}$). In other words, the IMD 102 can operate efficiently in discriminating the cardiac signal as VT or SVT using the initial threshold FCC value ($FCC_{TH1}$).

If the third highest FCC value ($FCC_{3H,SVT}$) is significantly different from the initial threshold value ($FCC_{TH1}$), the method 1400 proceeds to 1412. At 1412, the method 1400 can allow retrieval of EGM and/or FCC values from a past VT episode of the patient available in the memory 206. At 1414, FCC values of each beat for the last ten beats in the VT event can be computed. At 1416, a third highest FCC value ($FCC_{3H,VT}$) amongst the computed FCC values of the VT episode can be determined. As indicated in the FIG. 15, FCC values of the last ten beats of the VT event are computed and are shown on a linear scale as FCC values VT1-VT10. The FCC values of the VT event are shown as arranged in an increasing order in which the FCC value VT1 is the highest value and the FCC value VT10 is the lowest value amongst the computed FCC values for the VT. As illustrated in the FIG. 15, the FCC value VT3 is the third highest FCC value ($FCC_{3H,VT}$) amongst the various FCC values computed for the last 10 beats in the VT episode.

At 1418, a decision is made to determine as to whether the third highest FCC value ($FCC_{3H,VT}$) of the VT episode is greater than or equal to the third highest FCC value ($FCC_{3H,SVT}$) of the SVT event. If the third highest FCC value ($FCC_{3H,VT}$) of the VT episode is greater than or equal to the third highest FCC value ($FCC_{3H,SVT}$) of the SVT event, the method 1400 proceeds to 1410, and the method 1400 recommends the initial threshold value ($FCC_{TH1}$) as the recommended threshold value ($FCC_{TH2}$) for the discrimination programmable parameter. If the third highest FCC value ($FCC_{3H,VT}$) of the VT episode is smaller than the third highest FCC value ($FCC_{3H,SVT}$) of the SVT event, the method 1400 proceeds to 1420.

At 1420, a difference between the FCC value ($FCC_{3H,SVT}$) and the FCC value ($FCC_{3H,VT}$) is determined such as to compute a range for a second threshold value ($FCC_{TH2}$) of the discrimination programmable parameter. This difference between the two FCC values is indicated as lamda ($\lambda$) in FIG. 14. At 1422, a variable delta ($\delta$) is determined such that a condition $0<\delta<\lambda$ can be satisfied. At 1424, the method 1400 can compute the second threshold FCC value ($FCC_{TH2}$) by subtracting $\delta$ from the initial threshold FCC value ($FCC_{TH1}$). As a result, the second threshold FCC value ($FCC_{TH2}$) is between $FCC_{3H,SVT}$ and $FCC_{3H,VT}$, i.e., $FCC_{3H,VT}<FCC_{TH2}<FCC_{3H,SVT}$. In an arrhythmia discrimination algorithm that classifies an arrhythmia as SVT if at least three out of ten beats have FCC values that are greater than or equal to the FCC threshold, using the recommended second threshold value $FCC_{TH1}$ can cause the generated SVT event to be correctly classified as SVT (because there are three FCC values greater than $FCC_{TH2}$, as illustrated in FIG. 15), while at the same time to cause the VT event to be correctly classified as VT (because there are less than three FCC values greater than $FCC_{TH2}$, as illustrated in FIG. 15). By contrast, using the initial threshold FCC value ($FCC_{TH1}$) would have caused the generated SVT event to be incorrectly classified as VT (because there are only two FCC values greater than $FCC_{TH1}$). As a result, the method 1400 can recommend the threshold FCC value based on the analysis of the VT event and the SVT event.

In various examples, the methods and systems can compute an optimal threshold FCC value for the programmable parameter by allowing the physician to initiate an analysis cycle for the SVT event and/or VT event. The second threshold FCC value for the programmable parameter can be computed based on the analysis of the identified characteristics of the physiological signal sensed during these events. Accordingly, the IMD 102 can be configured to discriminate the cardiac signals using the newly computed second threshold FCC value.

At least some of the examples disclosed in this document can facilitate in determining the patient specific threshold values (e.g., FCC values) thr the programmable parameter. Typically, the IMD 102 can be configured to discriminate the cardiac signal as VT or SVT using a threshold FCC value. If the FCC value of the cardiac signal is greater than the threshold FCC value, the BID 102 discriminates the cardiac signal as an SVT beat. If a significant number of beats are classified as SVT beats (e.g., at least 3 out of 10 beats are SVT beats), the rhythm is classified as SVT rhythm, and the IMD 102 inhibits the VT therapy. If the FCC value of the cardiac signal is smaller than the threshold FCC value, the IMD 102 discriminates the cardiac signal as a VT beat. If a significant number of beats are classified as VT beats (e.g., at least 8 out of 10 beats are VT beats), the rhythm is classified as VT rhythm, and the IMD 102 initiates the VT therapy. However, the threshold FCC value can be patient specific. In other words, the threshold FCC value for one patient may be different than the threshold FCC value of the other patient.

In an example, the SVT events can be generated and the FCC values of the one or more beats of the SVT event can be measured such as to determine the threshold value that is specific to the patient. For example, the methods and systems disclosed herein can be configured to analyze the SVT events and compute the FCC values of the last ten beats of the SVT event. The third highest FCC value from the computed FCC values of the SVT event can be selected and a decision is made such as to determine whether the initial threshold FCC value is an optimal value for discriminating a cardiac signal as SVT. Although the third highest FCC value is chosen for the determination process, the methods can select any other FCC value from the computed FCC values of the last ten beats without any limitations. In general, for example, in an arrhythmia discrimination algorithm that classifies a rhythm as SVT if at least M out of N beats have FCC values greater than the FCC threshold value, the optimal value for FCC threshold can be determined using the M-th highest FCC value out of the N beats. In other scenarios, the method can employ various statistical or mathematical calculations to the FCC values of a specified number of beats to select the FCC value for determining an optimal value for FCC threshold.

On selection of the particular FCC value from the SVT event, the method can be configured to determine the difference between the selected FCC value and the initial threshold value of the discrimination programmable parameter. If the two values are not significantly different, then the method can be configured to recommend the initial threshold value as the recommended threshold value for the programmable parameter. This means that the initial threshold value is appropriate for the patient and the IMD 102 can precisely provide or inhibit the VT therapy on detection of the VT or SVT using the initial threshold value. If the two values are significantly different and the selected FCC value is greater than the initial threshold value, the method can still be configured to recommend the initial threshold value as the recommended threshold value for the programmable parameter.

However, if the two values are significantly different and the selected FCC value is smaller than the initial threshold value, then the method can compute a second threshold value on the basis of the selected FCC value from the SVT event. Accordingly, the method can be configured to recommend the newly computed threshold value. An advantage of recommending a lower threshold value is that RID 102 can now classify those future cardiac signals as SVT which otherwise would have been mis-classified as VT. For example, if the initial threshold value is 0.94, then all cardiac signals having FCC value lesser than the threshold value of 0.93 can be classified as VT and accordingly the IMD 102 can initiate the VT therapy. For example, it is determined that the threshold FCC value for this particular patient should be 0.92 rather than 0.94 after analyzing a trend of FCC values obtained from the SVT events of this patient. Clearly, with the newly computed threshold value, the IMD 102 can now classify the future cardiac signals having FCC value greater than 0.92 as SVT and inhibit the VT therapy. More specifically, the IMD 102 can now classify all those cardiac signals having FCC values in between 0.92-0.94 as SVT using the newly computed threshold FCC value which otherwise would have been classified as VT. As a result, the method facilitates in determining an optimum threshold value for the programmable parameter so that the BID 102 can inhibit the VT therapy delivery in response to cardiac signals that can be incorrectly classified as VT if the initial threshold FCC value is used.

As these changes in the threshold value of the programmable parameter can occur in the presence of the physician, the patient can no longer be given erroneous therapies. The optimal selection of the threshold value can ensure providing only necessary therapies (e.g., VT therapy) to the patient and thereby, prevent battery drainage of the IMD 102 resulting in an increase in the life of the MD 102.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. The code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   implementing an arrhythmia discrimination algorithm, wherein the arrhythmia discrimination algorithm discriminates between supraventricular tachycardia (SVT) and ventricular tachycardia (VT) using a programmable parameter programmed to a first threshold value;
   sensing a physiological signal during a known SVT event, and identifying characteristics of the sensed physiological signal;
   automatically programming the programmable parameter to a second threshold value, the second threshold value determined using the identified characteristics of the sensed physiological signal; and
   classifying a cardiac signal as either an SVT or a VT using the arrhythmia discrimination algorithm with the programmable parameter programmed to the second threshold value.

2. The method of claim 1, further comprising inducing the SVT event, wherein sensing the physiological signal includes sensing the physiological signal during the induced SVT event.

3. The method of claim 2, wherein inducing the SVT event includes:
   programming a cardiac stimulation sequence with specified values for stimulation parameters, wherein the stimulation parameters include at least one of a duration, a pulse width, a frequency, or an amplitude; and
   delivering the programmed cardiac stimulation sequence to a heart.

4. The method of claim 2, wherein inducing the SVT event includes:
   programming a neural stimulation sequence with specified values for stimulation parameters, wherein the stimulation parameters includes at least one of a duration, a pulse width, a frequency, or an amplitude; and
   delivering the programmed neural stimulation sequence to an autonomic neural target.

5. The method of claim 1, further comprising simulating the SVT event, wherein sensing the physiological signal includes sensing the physiological signal during the simulated SVT event.

6. The method of claim 5, wherein simulating the SVT event includes:
   programming a cardiac pacing sequence with a specified cardiac pacing mode and a pacing rate higher than a normal resting heart rate of a patient; and
   delivering the cardiac pacing sequence to the heart.

7. The method of claim 1, wherein the known SVT event includes a recorded intrinsic SVT event.

8. The method of claim 1, wherein:
the sensed physiological signal includes a plurality of segments;
the identified characteristics of the physiological signal include a morphological similarity metric between the plurality of segments and a template morphology; and
the template morphology is determined from a specified type of rhythm selected from a group of rhythms consisting of a normal sinus rhythm (NSR); an SVT; and a VT.

9. The method of claim 1, wherein:
the arrhythmia discrimination algorithm includes a morphology-based rhythm classification, the morphology-based rhythm classifier comprising a morphology similarity metric and a programmable morphology similarity threshold;
classifying the cardiac signal includes determining a cardiac depolarization morphology from the cardiac signal;
the programmable parameter of the arrhythmia discrimination algorithm includes the programmable morphology similarity threshold between the cardiac depolarization morphology and a template morphology; and
the template morphology is determined from a specified type of rhythm selected from the group of rhythms consisting of an NSR; an SVT; and a VT.

10. The method of claim 9, wherein:
the cardiac depolarization morphology includes a plurality of cardiac signal features extracted from the cardiac signal;
the template morphology includes a plurality oft late features stored in a memory; and
the morphological similarity metric includes a measure of correlation between the extracted cardiac signal features and the template features.

11. A system, comprising:
an arrhythmia discriminator configured to implement an arrhythmia discrimination algorithm to discriminate between ventricular tachycardia (VT) and supraventricular tachycardia (SVT) using a programmable parameter programmed to a first threshold value;
an SVT event analyzer configured to sense a physiological signal during a known SVT event and identify characteristics of the sensed physiological signal; and
a controller configured to:
determine a second threshold value for the programmable parameter using the identified characteristics of the sensed physiological signal;
automatically program the programmable parameter to the second threshold value; and
classify a cardiac signal as either an SVT or a VT using the arrhythmia discriminator with the programmable parameter programmed to the second threshold value.

12. The system of claim 11, wherein:
the controller is further configured to induce an SVT event; and
the SVT event analyzer is further configured to sense the physiological signal during the induced SVT event.

13. The system of claim 12, wherein the controller is configured to induce the SVT event, the induction of the SVT event includes delivering a programmed cardiac stimulation sequence to a heart.

14. The system of claim 12, wherein the controller is configured to induce an SVT event, the induction of the SVT event includes delivering a programmed neural stimulation sequence to an autonomic neural target.

15. The system of claim 11, wherein:
the controller is further configured to simulate an SVT event; and
the SVT event analyzer is further configured to sense the physiological signal during the simulated SVT event.

16. The system of claim 15, wherein the controller is configured to simulate an SVT event, the simulating an SVT event includes delivering a programmed cardiac pacing sequence to a heart.

17. The system of claim 11, wherein:
the controller is further configured to record an intrinsic SVT event; and
the SVT event analyzer is further configured to analyze the recorded intrinsic SVT event.

18. The system of claim 11, wherein the SVT event analyzer is further configured to:
extract a plurality of physiological signal segments from the physiological signal;
determine a template morphology from a specified type of rhythm selected from a group of rhythms consisting of a normal sinus rhythm (NSR); an SVT; and a VT; and
characterize the physiological signal by computing a morphological similarity metric between the plurality of physiological signal segments and the template morphology.

19. The system of claim 11, wherein:
the arrhythmia discriminator includes a morphology-based arrhythmia classifier, the morphology-based arrhythmia classifier comprising a morphology similarity metric and a programmable morphology similarity threshold; and
the controller is configured to:
determine a cardiac depolarization morphology from the cardiac signal;
determine a template morphology from a specified type of rhythm selected from a group of rhythms consisting of an NSR; an SVT; and a VT;
determine the second threshold value for the programmable morphology similarity threshold using the morphological similarity metric; and
classify the cardiac signal as either an SVT or a VT using the arrhythmia discriminator with the programmable morphology similarity threshold programmed to the second threshold value.

20. The system of claim 19, wherein the controller is further configured to:
extract a plurality of cardiac signal features from the cardiac signal;
retrieve a plurality of template features stored in a memory;
compute a correlation between the plurality of cardiac signal features and the plurality of template features; and
classify the cardiac signal as either an SVT or a VT using the correlation.

* * * * *